US007230699B1

United States Patent
Liphardt et al.

(10) Patent No.: US 7,230,699 B1
(45) Date of Patent: Jun. 12, 2007

(54) SAMPLE ORIENTATION SYSTEM AND METHOD

(75) Inventors: Martin M. Liphardt, Lincoln, NE (US); Ping He, Lincoln, NE (US)

(73) Assignee: J.A. Woollam Co., Inc., Lincoln, NE (US)

( * ) Notice: Subject to any disclaimer, the term of this patent is extended or adjusted under 35 U.S.C. 154(b) by 522 days.

(21) Appl. No.: 10/652,696

(22) Filed: Sep. 2, 2003

Related U.S. Application Data

(60) Provisional application No. 60/459,690, filed on Apr. 3, 2003, provisional application No. 60/418,266, filed on Oct. 15, 2002.

(51) Int. Cl.
*G01J 4/00* (2006.01)
(52) U.S. Cl. .................................................. 356/364
(58) Field of Classification Search ................ 356/369, 356/699, 399–400, 153, 156
See application file for complete search history.

(56) References Cited

U.S. PATENT DOCUMENTS

| | | | |
|---|---|---|---|
| 4,373,817 A | 2/1983 | Coates | 356/384 |
| 4,834,539 A * | 5/1989 | Le Bris et al. | 356/369 |
| 5,042,951 A * | 8/1991 | Gold et al. | 356/369 |
| 5,045,704 A | 9/1991 | Coates | 250/372 |
| RE34,783 E | 11/1994 | Coates | 250/372 |
| 5,486,701 A | 1/1996 | Norton et al. | 250/372 |
| 5,596,411 A | 1/1997 | Fanton et al. | 356/369 |
| 5,608,526 A | 3/1997 | Piwonka-Corle et al. | 356/369 |
| 5,793,480 A * | 8/1998 | Lacey et al. | 356/73 |
| 5,889,593 A | 3/1999 | Bareket | 356/445 |
| 5,900,939 A | 5/1999 | Aspnes et al. | 356/369 |
| 5,910,842 A * | 6/1999 | Piwonka-Corle et al. | 356/369 |
| 6,297,880 B1 * | 10/2001 | Rosencwaig et al. | 356/369 |
| 6,320,657 B1 * | 11/2001 | Aspnes et al. | 356/369 |
| 6,600,560 B2 | 7/2003 | Mikkelsen et al. | 356/369 |
| 6,940,592 B2 * | 9/2005 | Borden et al. | 356/326 |
| 2002/0024668 A1 | 2/2002 | Stehle et al. | |
| 2002/0033945 A1 * | 3/2002 | Xu et al. | 356/369 |

OTHER PUBLICATIONS

PCT Wo 99/45340 Kla-Tencer.

* cited by examiner

*Primary Examiner*—Tarifur Chowdhury
*Assistant Examiner*—Isiaka O. Akanbi
(74) *Attorney, Agent, or Firm*—James D. Welch

(57) ABSTRACT

Disclosed is a system comprising a stage with "X", "Y" and "Z" translation and "X", "Y" and optionally "Z" axes rotation capability, in combination with interrogation and monitoring means which act in functional combination to orient the surface of a sample so as to set an intended oblique approach of an electromagnetic beam with respect to a sample surface at a monitored location thereon.

2 Claims, 2 Drawing Sheets

SAMPLE ORIENTATION SYSTEM AND METHOD

This Application Claims Benefit of Provisional Applications Nos. 60/418,266 Filed Oct. 15, 2002 and 60/459,690 Filed Apr. 3, 2003.

TECHNICAL AREA

The disclosed invention relates to systems for applying electromagnetic beams to samples and more particularly to a system comprising a stage with "X", "Y" and "Z" translation and "X", "Y" and optionally "Z" axes rotation capability, in combination with interrogation and monitoring means which act in functional combination to orient the surface of a sample so as to set an intended electromagnetic beam angle of incidence and an azimuthal angle with respect to instrument, and a polarization coordination system at a monitored location thereon.

BACKGROUND

The practice of ellipsometry requires that a beam of electromagnetic radiation impinge on a sample surface at a known oblique angle-of-incidence thereto. Where a sample surface is smooth it is generally not difficult to orient said sample so that the surface thereof generally faces in a know direction, thereby enabling the relatively easy orienting of the beam with respect thereto. This can be accomplished, for instance, by aligning a sample so that a typically collimated beam of electromagnetic radiation reflects directly 180 degrees therefrom using known technology, and then rotating said beam a known number of degrees. Where a sample surface is not smooth, however, irregularities thereof affect the actual angle, and plane of incidence of a fixed direction beam which is achieved from point to point thereon. It is also noted that unlike where a normal incidence beam is used, correlation between sample tilt and sample height can occur when a beam approaches the surface of a sample at an oblique angle. It should therefore be appreciated where a sample surface is not smooth, it becomes important to be able to identify, (preferably using a beam applied along a normal incidence), and correct for sample surface irregularities at a location thereupon which is being investigated.

A known approach to accomplishing point to point corrections of an angle-of-incidence involves placing a sample onto a stage which allows "X", "Y" and "Z" translation capability as well as rotation capability around "X" and "Y axes and making adjustments to the orientation of a sample while directing a beam of electromagentic radiation downward, (as said system is viewed in elevation), onto a reflective objective located vertically above said sample so that said beam is caused to reflect therefrom over 360 degrees to a spherical mirror, onto a location on a sample to be investigated. Also present under said convex mirror is a prism which serves to direct an interrogation beam of electromagnetic radiation which approaches from the side, downward to the same spot on said sample being investigated. When said interrogation beam is caused to be reflected from the surface of the sample directly back through said prism, along the incident trajectory, it is determined that the sample surface at the point at which the interrogation beam interacts therewith is facing upward. While clever, it is noted that reflective optics are typically more expensive than refractive objectives and have a fixed focal length. On the other hand, refractive objectives with easily adjustable focal lengths, (ie. zoom lenses), are readily available and allow varying the viewing area of a sample.

While a specific Search was not conducted, known Patents are disclosed to aid the Examination:
Patent to Coates U.S. Pat. No. 4,373,817;
Patent to Coates U.S. Pat. No. 5,045,704;
RE. 34,783 to Coates;
Patent to Mikkelsen et al., U.S. Pat. No. 6,600,560;
Patent to Fanton et al., U.S. Pat. No. 5,596,411;
Patent to Piwonka-Corle et al., U.S. Pat. No. 5,910,842;
Patent to Piwonka-Corle et al., U.S. Pat. No. 5,608,526;
Patent to Bareket, U.S. Pat. No. 5,889,593;
Patent to Norton et al., U.S. Pat. No. 5,486,701;
Patent to Aspnes et al., U.S. Pat. No. 5,900,939;
PCT Application Publication WO 99/45340;
Published Application of Stehle et al., No. US2002/ 0024668 A1;

A need for a system which accomplishes point to point sample surface orientation and which also enables observing the sample surface generally from above, at various user adjustable magnifications, is thus identified.

DISCLOSURE OF THE INVENTION

The disclosed invention is a system for controlling the angle of incidence and angle of azimuth at which a beam of electromagnetic radiation obliquely impinges on a monitored location of a surface of a sample which comprises a sample supporting stage which can be translated in "X", "Y" and "Z" directions as well as rotated about "X", "Y" and optionally "Z" axes. (Note that this is to be interpreted to include rotating and translating the ellipsometer such that relative positioning of the sample and ellipsometer is achieved). Vertically, as viewed in side elevation, above said stage there is a first beam splitter means, a lens and a first camera means for providing a view of a portion of the surface of said sample, said first beam splitter means having optionally positioned below a lower surface thereof, light emitting means for providing light to the surface of said sample. Laterally with respect to said first beam splitter means there being a reflection means, and vertically above said reflection means there being a second beam splitter. Vertically above said second beam splitter there is a second camera means and laterally with respect to said second beam splitter, there is sequentially a lens and an essentially point source of electromagnetic radiation. Said first and second camera means each have associated therewith display means. Said system further comprises an ellipsometer polarization state generator to cause, and a polarization stage detector to monitor, a beam of electromagnetic radiation which in use impinges on said monitored location on said surface of said sample at an oblique angle thereto. In use said first camera means and its associated display means provide a view of at least a portion of the surface of a sample utilizing light provided by said light emitting means for providing light to the surface of said sample positioned on said lower surface of said first beam splitter, and said essentially point source of a source of electromagnetic radiation provides electromagnetic radiation to the surface of said sample via said second beam splitter, said reflective means and said first beam splitter. Said sample supporting stage is caused to be translated in any of said "X", "Y" and "Z" directions as well as rotated about said "X", "Y" and optionally "Z" axes which are necessary to cause an interrogating beam of electromagnetic radiation provided by said essentially point source, (eg. a fiber optic), of a source of electromagnetic radiation to reflect from the surface of said sample, proceed back through said first beam splitter means, reflect from said reflective means, pass through said second beam splitter means, enter said second camera means and cause an image on the display means associated therewith which indicates, (eg. via an electronically generated crosshair), that the monitored location on the sample surface is oriented so as to face substantially vertically. The purpose is to align said sample surface to assure that said beam of electromagnetic radiation provided to said monitored location on the surface of said sample at an oblique angle approaches said surface at a known intended angle of incidence thereto, rather than at an angle of incidence which is modified by surface irregularities or non-flat samples, (eg. wedge shaped).

A problem can develop in that an interrogation beam spot can appear in the image of the first camera means display as part of the interrogation beam can proceed through said first beam splitter thereinto. As a solution to this problem, said system can further provide that a polarizer means be placed into the path of said beam of electromagnetic radiation provided by said essentially point source of a source of electromagnetic radiation, and in which said first beam splitter is sensitive to polarization state. The polarizer means is preferable adjustable to enable changing the direction of imposed polarization. This can be beneficial where, for instance, the sample has an effect on the reflected interrogation beam polarization state, and where it is determined desirable to allow some of said interrogation beam to reach the first camera means, (eg. where it is found to aid with sample surface alignment).

It is noted as an introduction to the method of the disclosed invention that when the sample surface is oriented to face substantially vertically at said monitored location, limited range "X" and/or "Y" translation has essentially no effect on said image on the display means associated with said second camera means, thereby indicating that the monitored location on said sample surface is oriented so as to face substantially vertically over said limited range of "X" and "Y" translation. (It is noted that a standard ellipsometer alignment detector means is used to achieve this step). Of course gross "X" and/or "Y" translation does have an effect which is representative of surface irregularities.

It is noted that a sample with surface irregularities was used as an example in the foregoing, but the sample can also be very small, (eg. millimeter dimensions), which presents similar alignment difficulties.

The method of calibration involving orientating a monitored location on a sample, said sample being characterized by:
  it has surface irregularities, or
  it is small in dimension;

comprises the steps of:
  a) providing a stage for supporting a sample, said stage having means for effecting translation in any of said "X", "Y" and "Z" directions as well as rotation about said "X", "Y" and optionally "Z" axes;
  b) placing a sample characterized by a selection from the group consisting of:
    it has surface irregularities,
    it is small in dimension;
  onto surface onto said stage;
  c) causing an interrogating beam of electromagnetic radiation to impinge on said monitored location on said sample;
  d) monitoring the effect of "X" and "Y" direction translation on the locus of reflected beam electromagnetic radiation from the surface said sample and if either said translation causes significant change therein practicing step e, and if neither said translation causes significant change therein terminating the practice of said method;
  e) adjusting rotation of said stage about at least one of the "X" and "Y" directions and again monitoring practicing step d.

Said method of calibration can further comprises at least one "Z" direction translation to better enable monitoring the effect of "X" and "Y" direction translation on the locus of reflected beam electromagnetic radiation from the surface of said sample.

The invention will be better understood by reference to the Detailed Description Section of this Specification, with reference to the Drawings.

SUMMARY

It is an objective and/or purpose of the disclosed invention to provide a system for aligning a sample system and controlling the angle and plane of incidence at which a beam of electromagnetic radiation obliquely impinges on a monitored location of a surface of a sample.

It is another objective and/or purpose of the disclosed invention to provide a method of calibration of ellipsometer and the like systems involving orientating a monitored location on a sample which presents with a surface having irregularities.

Other objectives and/or purposes of the disclosed invention will become apparent upon a reading of the Specification and Claims.

DETAILED DESCRIPTION

Figures 1, 2:
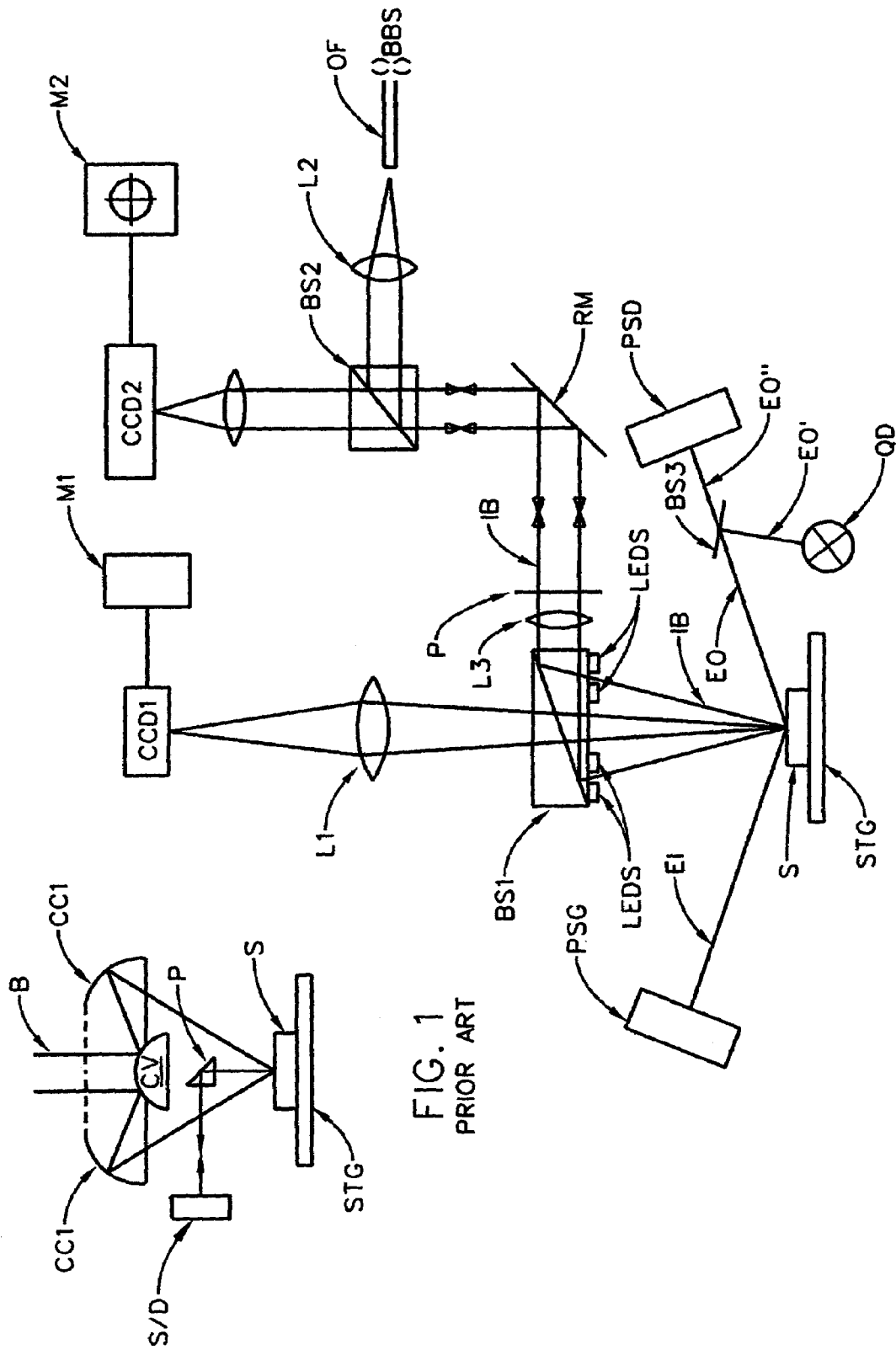
FIG. 1 shows a prior art system for controlling the angle of incidence at which a beam of electromagnetic radiation obliquely impinges on a monitored location of a surface of a sample.
FIG. 2 shows the disclosed system for controlling the angle of incidence at which a beam of electromagnetic radiation obliquely impinges on a monitored location of a surface of a sample.

Turning now to the Drawings, FIG. 1 shows a known prior art system for controlling the angle of incidence at which a beam of electromagnetic radiation obliquely impinges on a monitored location of a surface of a sample. Said known approach to accomplishing point to point corrections of an angle-of-incidence involves placing a sample (S) onto a stage (STG) which allows "X", "Y" and "Z" translation capability as well as rotation capability around "X" and "Y" axes and making adjustments to the orientation of a sample while directing a beam of electromagentic radiation downward, (as said system is viewed in elevation), onto a convex mirror (CV) located vertically above said sample so that said beam is caused to reflect therefrom in all directions over 360 degrees via reflection by an appropriately located spherical mirror (CC1), onto a location on a sample (S) to be investigated. Also present under said convex mirror (CV) is a prism (P) which serves to direct an interrogation beam of electromagnetic radiation which approaches from the side from a source/detector mens (S/D), downward to the same spot on said sample being investigated. When said interrogation beam is caused to be reflected from the surface of the sample directly back through said prism (P), along the incident trajectory, it is determined that the sample surface at the point at which the interrogation beam interacts therewith is facing upward.

FIG. 2 shows that the disclosed invention is a system for controlling the angle of incidence at which a beam of electromagnetic radiation (EI) obliquely impinges on a monitored location of a surface of a sample (S) which is present on a sample supporting stage (STG) which can be translated in "X", "Y" and "Z" directions as well as rotated about "X", "Y" and optionally "Z" axes. Vertically, as viewed in side elevation, above said stage (STG) there is a first beam splitter means (BS1), a Zoom lens (L1) and a first camera means (CCD1) for providing a view of a portion of the surface of said sample (S), said first beam splitter (BS1) means optionally having positioned on a lower surface thereof light emitting means (LEDS) for providing light to the surface of said sample (S). Laterally with respect to said first beam splitter means (BS1) there being a reflection means (RM), and vertically above said reflection means (RM) there being a second beam splitter (BS2). Vertically above said second beam splitter (BS2) there is a second camera means (CCD2) and laterally with respect to said second beam splitter (BS2), there is sequentially a lens (L2) and an essentially point source of electromagnetic radiation which is shown as being an Optical Fiber (OF) which receives electromagnetic radiation from source (BBS). Said first (CCD1) and second (CCD2) camera means each have associated therewith display means (M1) and (M2) respectively. Said system further comprises an ellipsometer polarization state generator (PSG) to cause, and a polarization stage detector (PSD) to monitor, a beam (EI) of electromagnetic radiation which in use impinges on said monitored location on said surface of said sample at an oblique angle thereto. In use said first camera means (CCD1) and its associated display means provide a view of at least a portion of the surface of a sample (S) utilizing light provided by said light emitting means (LEDS) for providing light to the surface of said sample (S) and which are positioned on said lower surface of said first beam splitter (BS1), and said essentially point source of a source of electromagnetic radiation provides electromagnetic radiation to the surface of said sample via said second beam splitter (BS2), said reflective means (R) and said first beam splitter (BS1). Said sample supporting stage (STG) is caused to be translated in any of said "X", "Y" and "Z" directions as well as rotated about said "X", "Y" and optionally "Z" axes which are necessary to cause an interrogating beam (IB) of electromagnetic radiation provided by said essentially point source, (ie. fiber optic (OF)), of a source of electromagnetic radiation to reflect from the surface of said sample (S), proceed back through said first beam splitter (BS1) means, reflect from said reflective means (R), pass through said second beam splitter means (BS2), enter said second camera means (CCD2) and cause an image on the display means (M2) associated therewith which indicates that the monitored location on the sample (S) surface is oriented so as to face substantially vertically. The purpose is to align said sample (S) surface to assure that said beam of electromagnetic radiation (EI) provided to said monitored location on the surface of said sample (S) at an oblique angle approaches said surface at a known intended angle of incidence thereto at the exact point of impingement, rather than at an angle of incidence which is modified by surface irregularities.

A problem can develop in that an interrogation beam spot can appear in the image of the first camera means (CCD1) display (M1) as part of the interrogation beam can proceed through said first beam splitter (BS1) thereinto. As a solution to this problem, said system can further provide that a polarizer means (P) be placed into the path of said interrogation beam (IB) of electromagnetic radiation provided by said essentially point source of a source of electromagnetic radiation, and in which said first beam splitter (BS1) is sensitive to polarization state. The polarizer means (P) is preferable adjustable to enable changing the direction of imposed polarization. This can be beneficial where, for instance, the sample (S) has an effect on the reflected interrogation beam (IB) polarization state, and/or where it is determined desirable to allow some of said interrogation beam to reach the first camera means (CCD1), (eg. where it is found to aid with sample surface alignment).

Note that the ellipsometer system is shown to contain a Beam Splitter (BS3) and a Quad Detector (QD). Output Beam (EO) is caused partially to enter the (PSD) as (EO") and partially enter (QD) as (EO') thereby. "X" and "Y" translation of the sample (S) which cause the (AOI) of Input Beam (E1) to reflect from said Sample (S) at various (AOI) and (POI) angles show up at the (QD). When a Sample (S) is aligned so that a normal to its surface is directed vertically in the Laboratory Frame of Reference at the location of the Ellipsometer Beam (EI) impingment thereupon small "X" and/or "Y" translations have essentially no effect on the (QD) outputs. The ellipsometer Alignment means, (ie. (BS3) and (QD)), are then utilized in the alignment procedure.

Note, in the foregoing, the terminology Angle-Of-Incidence refers to the angle between the locus of a beam of electromagnetic radiation and a normal to a surface of a sample, and the terminology Plane-Of-Incidence refers to the plane formed by the Laboratory Normal the normal to the surface of the sample at and the locus of a beam of electromagentic radiation at a location thereupon being investigated.

Figure 3B:
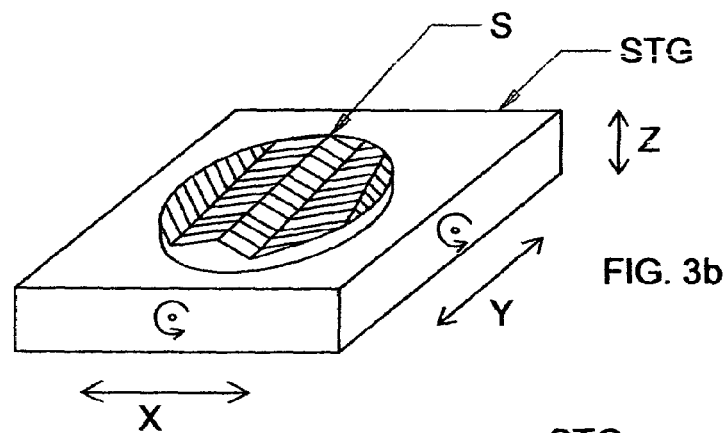
FIG. 3b shows the stage of FIGS. 2 and 3a with a sample having a non-uniform surface placed thereupon.
Figure 3A:
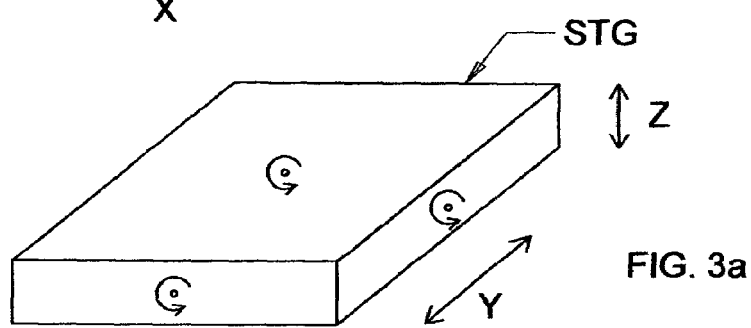
FIG. 3a shows a perspective view of the stage of FIG. 2 with indication that translation thereof in any of said "X", "Y" and "Z" directions as well as rotation about said "X", "Y" and optionally "Z" axes is possible.
Figure 4A:
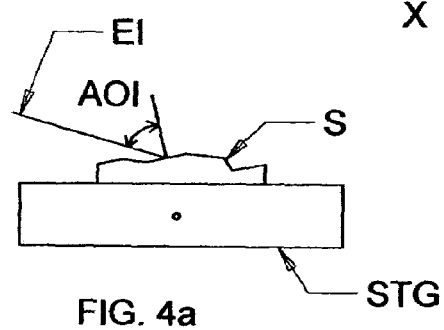
FIG. 4a shows show the sample in FIG. 3b in side elevation, and also showing the electromagentic beam (EI) of FIG. 2.
Figure 4B:
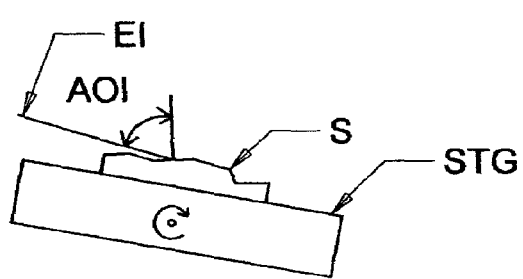
FIG. 4b shows show the configuration in FIG. 4a with the stage rotated about the "Y" axis so that a normal to the point on the sample upon which the beam (EI) impinges is oriented to project vertically.

Finally, it is again mentioned that the disclosed invention can be applied to samples with irregular surfaces and small dimension samples, both of which present similar surface alignment challenges. To demonstrate this, FIG. 3a is provided to show a perspective view of the stage (STG) identified in FIG. 2, with indication that translation thereof in any of said "X", "Y" and "Z" directions, as well as rotation about said "X", "Y" and optionally "Z" axes is possible. FIG. 3b shows the stage (STG) of FIGS. 2 and 3a with a sample (S) having a non-uniform surface placed thereupon. FIG. 4a shows show the sample (S) in FIG. 3b in side elevation, and also shows the electromagentic beam (EI) of FIG. 2 impinging thereupon. FIG. 4b shows show the configuration in FIG. 4a with the stage (STG) rotated about the "Y" axis so that a normal to the point on the sample (S) upon which the beam (EI) impinges is oriented to project vertically. The important point demonstrated in FIG. 4a is that the angle-of-incidence (AOI) beam (EI) makes with respect to the sample (S) surface is a true angle-of-incidence (AOI) which can be entered into an analysis of the sample.

The angle-of-incidence (AOI) demonstrated in FIG. 4a is not such a true angle-of-incidence (AOI) and the normal to the sample surface does not project vertically. Note also that the stage (STG) as shown in FIG. 4 can be translated in the "X" direction over some distance and the angle-of-incidence (AOI) remains the same. This effect is utilized in the steps c and d of the calibration procedure presented earlier in this Specification.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. A method of calibration involving orientating a monitored location on a sample, said sample being characterized by:
   it has surface irregularities, or
   it is small in dimension;
   comprising the steps of:
   a) providing a stage for supporting a sample, said stage having means for effecting translation in any of said "X", "Y" and "Z" directions as well as rotation about said "X", "Y" and optionally "Z" axes;
   b) placing a sample characterized by a selection from the group consisting of:
      it has surface irregularities,
      it is small in dimension;
      onto surface onto said stage;
   c) causing an interrogating beam of electromagnetic radiation to impinge on said monitored location on said sample;
   d) monitoring the effect of "X" and "Y" direction translation on the locus of reflected beam electromagnetic radiation from the surface said sample and if either said translation causes significant change therein practicing step e, and if neither said translation causes significant change therein terminating the practice of said method;
   e) adjusting rotation of said stage about at least one of the "X" and "Y" directions and again practicing step d.

2. A method of calibration as in claim 1, which further comprises at least one "Z" direction translation to better enable monitoring the effect of "X" and "Y" direction translation on the locus of reflected beam electromagnetic radiation from the surface of said sample.

* * * * *